United States Patent
Angeletti (10) Patent No.: US 9,965,702 B1
(45) Date of Patent: May 8, 2018

(54) METHOD FOR ANALYSIS AND INTERPRETATION OF FLOW CYTOMETRY DATA

(71) Applicant: Cesar Angeletti, Smyrna, GA (US)

(72) Inventor: Cesar Angeletti, Smyrna, GA (US)

( * ) Notice: Subject to any disclaimer, the term of this patent is extended or adjusted under 35 U.S.C. 154(b) by 0 days. days.

(21) Appl. No.: 15/391,049

(22) Filed: Dec. 27, 2016

(51) Int. Cl.
| G06K 9/00 | (2006.01) |
| G06K 9/62 | (2006.01) |
| G01N 15/14 | (2006.01) |
| G06K 9/46 | (2006.01) |
| G06T 11/20 | (2006.01) |
| G06F 19/24 | (2011.01) |
| G01N 15/00 | (2006.01) |
| G01N 15/10 | (2006.01) |

(52) U.S. Cl.
CPC ....... *G06K 9/6254* (2013.01); *G01N 15/1429* (2013.01); *G06F 19/24* (2013.01); *G06K 9/0014* (2013.01); *G06K 9/4642* (2013.01); *G06K 9/6256* (2013.01); *G06T 11/206* (2013.01); *G01N 2015/0065* (2013.01); *G01N 2015/1006* (2013.01); *G06T 2200/24* (2013.01); *G06T 2210/41* (2013.01)

(58) Field of Classification Search
None
See application file for complete search history.

(56) References Cited

U.S. PATENT DOCUMENTS

| 5,605,805 | A | 2/1997 | Verwer et al. |
| 6,954,722 | B2 | 10/2005 | Parks et al. |
| 7,522,758 | B2 | 4/2009 | Ortyn et al. |
| 8,214,157 | B2 | 7/2012 | Moser et al. |
| 8,682,810 | B2 * | 3/2014 | Zhang ................ G06K 9/00147 382/100 |
| 9,034,257 | B2 | 5/2015 | Covey et al. |
| 9,123,095 | B2 | 9/2015 | Lee et al. |
| 2008/0078567 | A1 * | 4/2008 | Miller ................. H01B 11/203 174/70 R |
| 2009/0097733 | A1 * | 4/2009 | Hero, III .............. G06K 9/6215 382/133 |
| 2009/0307248 | A1 * | 12/2009 | Moser .................. G06K 9/6298 |

(Continued)

FOREIGN PATENT DOCUMENTS

CN 103942415 7/2014

OTHER PUBLICATIONS

Bashashati, A.; et al. "A pipeline for automated analysis of flow cytometry data: preliminary results on lymphoma sub-type diagnosis." Sep. 2, 2009 p. 4946, 4947, 4948.

(Continued)

*Primary Examiner* — Nancy Bitar
(74) *Attorney, Agent, or Firm* — Bryan L. Baysinger; H. Artoush Ohanian (57) ABSTRACT

Disclosed are various embodiments for interpretation of flow cytometry data. Flow cytometry data sets are combined to form a multidimensional image cube. The machine learning functions and genetic algorithm interpret the multidimensional image cube to produce a confidence value that is assigned to a function for the targeted condition. The confidence value determines the relative degree to which a targeted condition is present or absent in a flow cytometry data set. Such confidence value can be used to diagnose and interpret results from flow cytometry data.

8 Claims, 4 Drawing Sheets

(56) References Cited

U.S. PATENT DOCUMENTS

2013/0124522 A1* 5/2013 Moser ............... G06K 9/6298
 707/737
2013/0226469 A1 8/2013 Robinson et al.
2016/0327779 A1* 11/2016 Hillman ............. G02B 21/367

OTHER PUBLICATIONS

Greg Finak; et al. "OpenCyto: An Open Source Infrastructure for Scalable, Robust, Reproducible, and Automated, End-to-End Flow Cytometry Data Analysis" Aug. 28, 2014 p. 4, 9-10, Figure 2, p. 5.

Saumyadipta Pyne; et al. "Automated high-dimensional flow cytometric data analysis" Apr. 3, 2009 p. 8520, 3522-8523.

Florian Mair; et al. "The end of gating? An introduction to automated analysis of high dimensional cytometry data" Jan. 2016 p. 37-38, 39.

Hernani D. Cualing "Automated analysis in flow cytometry" Apr. 15, 2000 p. 111, 112.

Courtot M. "flowCL: ontology-based cell population labelling in flow cytometry." Apr. 15, 2015 p. 1338.

Yuan, Cao; et al "UrineCART, a machine learning method for establishment of review rules based on UF-1000i flow cytometry and dipstick or reflectance photometer." Dec. 2012 p. 2-3, 5.

* cited by examiner

METHOD FOR ANALYSIS AND INTERPRETATION OF FLOW CYTOMETRY DATA

FIELD OF THE INVENTION

The present invention relates to a method and system for analysis and interpretation of flow cytometry data, utilizing a multidimensional cube engine, a pre-training engine, a training engine, and a machine-vision function.

BACKGROUND OF THE INVENTION

Flow cytometry is a technology that is used to analyze the physical and chemical properties of particles in a sheath fluid as it passes through one or more lasers. Most commonly cell particles are fluorescently labelled and then excited by the laser to emit light at varying wavelengths.

A flow cytometer has five main components. First, a fluid sheath is formed that carries and aligns cells so that they may pass single file through a light beam for sensing. Second, a measurement system, usually a laser beam in which the beam is aligned with the fluid sheath. Third, a detector and an analog to digital conversion system, which converts the analog measurements of forward-scattered light and side-scattered light from the laser beam into digital signals that can be processed by a computing system. Fourth, an amplification system, linear or logarithmic. Lastly, a computer system for analysis of the signals.

Flow cytometry is used in the diagnosis of health disorders, in particular blood cancers, but also has other applications in chemical research and analysis of properties of particles. Flow cytometers are capable of analyzing thousands of particles every second, and can actively separate and isolate particles having specific physical or chemical properties. The process of collecting data from samples using flow cytometry is called acquisition. Acquisition is mediated by a computer physically connected to the flow cytometer and receiving digital or analog signals from the flow cytometer. Modern flow cytometers typically have multiple lasers and detectors incorporated to detect multiple antibodies or markers on the surface of the particles.

Multi-parameter flow cytometry immunophenotyping, a technique used to study the protein expressed by cells, has become a method of choice for the differential diagnosis of reactive and neoplastic blood disorders. As known in the art, samples are tagged with monoclonal antibodies coupled to fluorescent labels in order to characterize the different cellular populations in a wide range biological specimens, including blood, bone marrow tissue, bodily fluids, and lymph nodes. Additionally, other flow cytometry phenotyping systems are known and disclosed, examples of such are quantum dot or isotope labeling, others are available and will occur to those of skill in the art.

Typically, several tens of thousands of cells are measured within a few seconds and stored as digital data. This data set represents an empirical look at the contents of the specimen based upon the biological markers encoded for.

Genetic Algorithms, examples of which are generally disclosed in U.S. Pat. Nos. 4,935,877, 5,255,345, 5,390,283, among others, which are incorporated herein by reference, are utilized to analyze flow cytometry data provided by conventional flow cytometry data collection methods.

GENIE™ is a Genetic Algorithm software system that accounts for rapidly evolving feature extraction algorithms for image analysis. Historically GENIE™ is utilized for feature extraction on aerial topographical and satellite imagery. GENIE™ is an evolutionary computation software system that uses a genetic algorithm to assemble image-processing tools from a collection of low-level image operators, such as edge detectors, texture measures, spectral operations, and other morphological features. Each image processing tool generates a number of feature planes, which are then combined using a supervised classifier (Fisher linear discriminant) to generate a final boolean feature mask. A population of image processing tools is generated, ranked according to a fitness metric measuring their performance on some user-provided training data, and fit members of the population permitted to reproduce.

GENIE™ uses several standard fitness metrics including Euclidean distance and Hamming distance. The process cycles until the population converges to a solution, or the user decides to accept the current best solution. GENIE may choose to ignore the spatial information in the image and rely wholly on spectral operations and the supervised classifier module, but in practice GENIE will construct integrated spatio-spectral algorithms.

GENIE's™ system architecture is designed to provide flexible and powerful computing paradigm. GENIE™ can search a rich and complex feature space using its gene pool of standard primitive image processing operators and the results of additional analyst-selected algorithms.

Machine learning teaches computers to learn from experiences. Machine learning algorithms use computational methods to learn information directly from data without relying on a predetermined equation as a model. The algorithms associated with machine learning improve their performance as the number of samples available for learning increases.

Typically, machine learning algorithms find natural patterns in data that generate insight and help make better decisions and predictions. Machine learning is used to make critical decisions in medical diagnosis, stock trading, energy load forecasting, and many more applications in which prediction from samples is possible.

Machine learning uses two types of techniques. Supervised learning is one type that trains a model on known input and output data so that it can predict future outputs. Unsupervised learning, the second type, finds hidden patterns or intrinsic structure within input data.

The goal of supervised machine learning is to build a model that makes predictions based on evidence in the presence of uncertainty. A supervised learning algorithm that a known set of input data and known responses to the data and trains a model to generate reasonable predictions for the response to new input data.

The goal of unsupervised learning is to find hidden patterns or intrinsic structure in data. It is used to find inferences from datasets consisting of input data without labeled responses. Clustering is the most common unsupervised learning technique. It is used for exploratory data analysis to find hidden patterns or groupings in data.

A genetic algorithm is a search heuristic that mimics the process of natural selection. Genetic algorithms use methods such as mutation and crossover to generate new genotype in the hope of finding good solutions to a given problem. Most recently machine learning techniques are used to improve the accuracy and performance of genetic algorithms.

Support vector machines (SVMs) are a set of related supervised learning methods used for classification and regression. Given a set of training examples each marked as belonging to one of two categories, an SVM training algorithm builds a model that predicts whether a new example falls into one category or the other.

An advancement of the current invention over traditional SVM analysis of flow cytometry data is the ability to measure multiple features or markers in one step without the need of pre-analytical feature selection operations in order to reduce dimensionality. It is well known that SVM's experience decreasing performance in supervised learning of data sets as the number of vectors or features increase. That problem often requires the addition of feature selection methods such as leave-one-out error and Kernel alignment. Genetic algorithms provide the ability to readily analyze multiple features or markers in a single training session, also allowing for a better understanding and prediction of multiple parameter data set prediction.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

In the following discussion, a general description of the method and system for analysis and interpretation of flow cytometry data and its components is provided.

Figure 1:
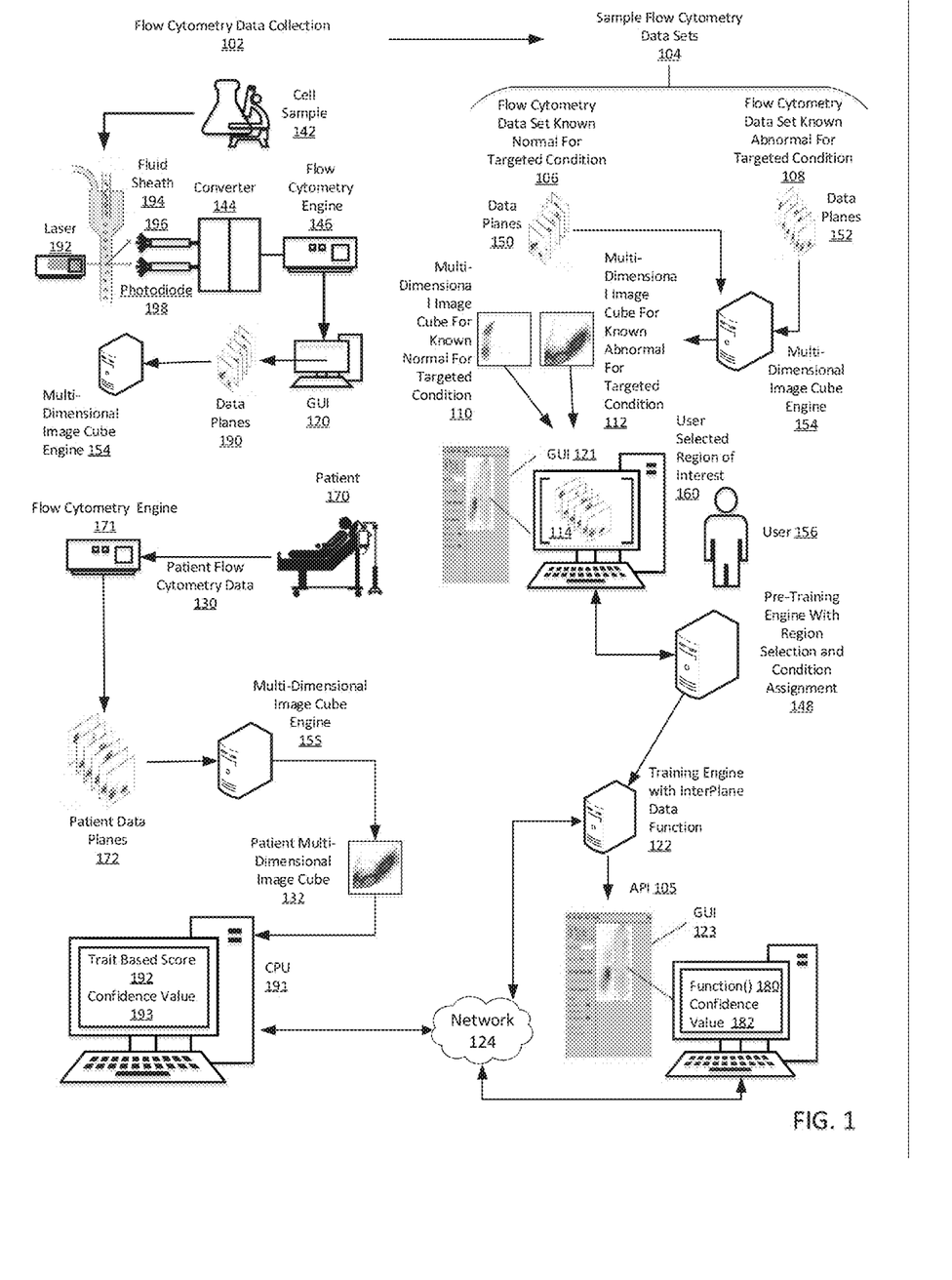
FIG. 1 is an overview of an example method and system of preparing a multidimensional image cube, training a machine-vision inter-plane data function for analysis of flow cytometry data, executing a trained function on patient flow cytometry data.

Flow cytometry data collection (102) involves numerous principles such as fluidic systems, optics and detection, signal processing, and electrostatic cell sorting. One of the fundamentals of flow cytometry is the ability to measure the properties of individual particles. When a sample enters a flow cytometer, the particles are randomly distributed in the three-dimensional space of the cell sample (142). The cell sample (142) is typically narrowed down to a single stream through a fluidics system with the application of hydro pressure. This stream is then passed through the one or more beams of light scattering or fluorescence emission. Lasers (192) typically serves as the light source in modern flow cytometers. The laser (192) produces a single wavelength of light that once contacted with the cell sample produces scattered light in the forward direction as a measure of cell size, scattered light in the side direction as a measure of cell complexity, and fluorescent light, also emitted in the side direction which is proportional to the relative amount of specific cellular surface, cytoplasmic and nuclear antigens. A photomultiplier tube or photodiode (196 and 198) receives light reflected from the cell. Light that originates from 0 to 20 degrees offset from the laser (192) excitation line is known as forward scatter light. Light measured at an angle of approximately 90 degrees to the excitation line of the laser (192) is called side scatter light and fluorescent signals. Both front scatter light and side scatter light are unique for every particle passing through the flow cytometer, and a combination of all are used to differentiate particles in the cell sample (142). Scattered and fluorescent emitted light signals are converted (144) to electronic pulses that are processed by the flow cytometry engine (146) and displayed on a graphical user interface "GUI" (120).

FIG. 1 sets forth a flow chart and a data flow diagram of an example of a system and method for processing a multidimensional image cube, training a machine-vision Inter-plane data function according to the Multidimensional image cube, and applying the trained function to a patient's flow cytometry data for diagnosis of a targeted condition. According to example embodiment set forth in FIG. 1, flow cytometry data collection (102) begins with the collection of a flow cytometry cell sample (142). In acquiring flow cytometry cell samples (142) scientists and clinicians follow flow cytometry protocols. Direct staining flow cytometry protocols is one of the most common staining methods, where live or fixed cells are incubated with directly labeled antibodies against cell surface antigens. Indirect staining flow cytometry is used if there is not a directly labeled antibody available, or if the goal is to amplify the signal already acquired. Indirect staining flow cytometry is where a cell is stained with a primary antibody against the antigen of interest and visualize using a labeled secondary antibody which recognizes the first, primary antibody. Other variants of staining are possible, as will be known by those of skill in the art, for instance, intracellular staining to be used when the antigen is not present on the cell surface.

Flow cytometry cell samples (142) are prepared by suspending single cells at a density of $10^5$-$10^7$ cells/ml in order to allow the cells to pass through the flow cytometer for reading. This concentration of cells is called the fluid sheath (194). The fluid sheath (194) influences the rate of flow sorting, which typically progresses at around 2,000-20,000 cells per second. The cell sample's (142) fluid sheath (194) is typically made of a phosphate buffered saline solution, but other solutions are available as will be known and understood by those skilled in the art.

The photomultiplier or photodiodes (196 and 198) contain optical filters to block certain wavelengths depending on the quantitative and qualitative measures sought from the cell sample (142). There are three common optical filter types. The long pass filter which allows light through an established cutoff point to an upward boundary. Short pass filter which permits light through the filter below an established boundary. Band pass filters which specify a certain range of wavelengths in which to receive light emission. In other embodiments a filter may not be used in collecting the analog data.

The converter (144) is the signal processing mechanism of flow cytometry that converts the analog signal received from the Laser (192) interacting with the fluid sheath (194) and subsequently received by the photodiodes (196 and 198).

According to the example embodiment in FIG. 1, the flow cytometry engine (146) conducts pulse processing at the time the particle passes through the laser (192) and emits to the photodiodes (196 and 198). The pulse processing triggers the events of when a particle is optimum for data reading. This pulse processing is used in conjunction with the signal reading acquired from the photodiodes (196 and 198) and converted into a digital signal by the converter (144) prior to processing in the flow cytometry engine (146). Other embodiments of converters (144) and flow cytometry engines (146) are capable of usage and will occur to those of skill in the art without differentiating from the disclosed invention.

According to the example embodiment in FIG. 1, the flow cytometry engine (146) processes and renders flow cytometry data planes (190), which display the relative proportions of cell markers per cell. The flow cytometry data planes (190) are then processed by the multidimensional image cube engine (154) by layering data planes on one another to form an multidimensional image cube (114) for display on a GUI (121). The multidimensional flow cytometry data planes (190) can be in two or more dimensions. The markers on a cell surface refer to fluorescent, radioactive, protein, or other type of marker normally utilized in flow cytometry data collection, as will occur to those of skill in the art.

According to the example embodiment of FIG. 1, the sample flow cytometry data sets (104) are grouped into normal for targeted condition (106) and abnormal for targeted condition (108). Normal for a targeted condition (106) consists of sample flow cytometry data sets (104) that are obtained from a known collection of patients all with known normal for a targeted condition flow cytometry data planes (150). Normal for a targeted condition (106) is not limited to what physicians or clinicians may deem healthy cell samples, but may consist of specific target cells or target isotopes that may be considered unhealthy. Abnormal for a targeted condition (108) consists of sample flow cytometry data sets (104) from samples that are known to have abnormal cells or markers that indicate the presence of the targeted condition. Normal and abnormal flow cytometry data sets are utilized to train the machine-vision inter-plane data function (122).

In the example embodiment of FIG. 1, normal data sets (106) and abnormal data sets (108) are input for the multidimensional image cube engine (154). The multidimensional image cube engine (154) accepts a specified series of normal or abnormal data planes (150 and 152) for processing to form multidimensional image cubes (110 and 112). The multidimensional image cube engine (154) accepts the bi-dimensional flow cytometry data planes in the form of TIFF image files and process the files together to form an image cube metafile such as FITS (Flexible Image Transport System), where each data plane pixel of x,y location is aligned in a third dimension z. FITS is a standardized data format widely used in processing of scientific images. FITS is designed specifically for scientific data and includes many provisions describing photometric and spatial calibration information within its metadata. A FITS metafile consists of a sequence of one or more Headers and Data Units (HDU's). A header is composed of ASCII card images usually read in a string array variable. The header describes the content of the associated data unit, which might be a spectrum, and image or tabular data in ASCII or binary format. FITS metafiles are written at the prompt level using specialized programming language such as IDL "Interactive Data Language". IDL is a data analysis platform most commonly associated with processing large amounts of scientific image data. Alternatively, FITS metafiles can be created using other languages such as C++ or Python.

In another example embodiment of FIG. 1, the data planes (150 and 152) consist of a density plot on an x and y axis grid. The multidimensional cube engine (154) processes the data planes (150 and 152) to form a three-dimensional image cube (110 and 112) of known normal and known abnormal multidimensional image cubes. In the example embodiment, the multidimensional cube engine (154) accepts variations of data such as raw data, TIFF, JPEG, EXIF, GIF, BMP, PNG, PPM, PGM, WebP, BAT, BPG, and others that will occur to those of skill in the art. The multidimensional image cube engine (154) then processes and renders the sample flow cytometry data planes (150 and 152) to form a multidimensional image cube for a known normal targeted condition (110) and a multidimensional image cube for a known abnormal targeted condition (112). The multidimensional image cube for a known normal targeted condition (110) is then displayed on a GUI (121) for user selection of the region of interest (160). Alternatively, the multidimensional image cube for a known normal targeted condition (110) is transmitted for processing in the pre-training engine for region selection and condition assignment (148). Similarly, the multidimensional image cube for a known abnormal targeted condition (112) is then displayed on a GUI (121) for user (156) selection of the region of interest (160). Alternatively, the multidimensional image cube for a known abnormal targeted condition (112) is transmitted for processing in the pre-training engine for region selection and condition assignment (148).

In an additional example embodiment of FIG. 1, the multidimensional image cube engine (154) processes normal and abnormal data planes (150 and 152) forming a multidimensional image cube for known normal (110) and abnormal (112) for the targeted condition. The multidimensional image cube engine (154) then processes and combines the known normal (110) and known abnormal (112) multidimensional image cubes for a targeted condition to form a composite multidimensional image cube (114). The composite multidimensional image cube (114) is displayed on a GUI (121) wherein region selection and condition assignment is processed on the pre-training engine with region selection and condition assignment (148). The pre-training engine with region selection and condition assignment (148) in the present example embodiment uses a best fit analysis to target the area of greatest concentration for region selection and condition assignment. Other embodiments of region selection and condition assignment are possible and will occur to those of skill in the art.

The GUI (121) displays each multidimensional image cube, where a user (156) can select a region of interest (160) for the training engine with inter-plane data function( ) (122) to set focalized boundaries on the input data within the GUI (121) and assigns positive or negative for the targeted condition in the selected areas of each multidimensional image cube (FITS metafiles). Once the area is selected and condition is assigned, the training engine creates a training multidimensional image cube metafile that is either normal for targeted condition or abnormal for targeted condition. The training metafiles consists a multidimensional image cube restricted to the selected area of interest with the assignment of positive or negative for the targeted condition. In further accordance with the example embodiment in FIG. 1, the multidimensional image cube metafiles are introduced into the training engine (122) that executes a selection function dependent upon the input data received from the training multidimensional image cube metafiles. This process requires at least one training metafile positive for the targeted condition and at least one training metafile negative for the targeted condition being introduced into the training engine (122). In the example embodiment the selection of region of interest (148 and 160) is not a required step, and positive or negative for the targeted condition can be assigned to the entire multidimensional image cube (114). The region selection assists the training engine (122) in providing greater accuracy and saves compute time when executing the machine-vision inter-plane data function( ) (122).

In accordance with the example method in FIG. 1, the training engine (122) tests machine-vision inter-plane data functions( ) and executes until a confidence value (182) is reached. One embodiment of a machine-vision inter-plane data function is a genetic algorithm "GA" that accepts input from training metafiles, to perform a metaheuristic optimization and search on the underlying TIFF image. This can be processed by executing any number of publicly available GA search software, for example GENIE™ software available at http://genie.lanl.gov. The GA executed by GENIE™ looks for a linear mathematical algorithm with maximum fitness to the selected areas of the training metafiles by iteration of mathematical operations on the multidimensional image cube TIFF file and extrapolating candidate solutions, until a final candidate solution reaching a threshold fitness returns (182).

The training engine with machine-vision inter-plane data function is connected to a network (124) wherein the confidence values (182) and produced functions (180) are available for input to a CPU (191). The connection to the network (124) and to a terminal or other GUI (123) occurs through a set of API's (105) and facilitate access to the engines. Other methods of connection and data transfer protocols are disclosed and are known to those of skill in the art. In accordance with the example embodiment of FIG. 1, the network (124) is cloud based. In other example embodiments the network (124) can consist of a LAN based network residing on a local Intranet. Other types of data networks are possible and will occur to those of skill in the art.

As set forth in the example embodiment of FIG. 1, a patient (170), having collected flow cytometry data (130), the patient flow cytometry data (130) is entered as input into the flow cytometry engine (171) to produce patient data Planes (172). The patient data planes (172) input into the multidimensional image cube engine (155), wherein the data planes (172) are converted into a patient's multidimensional image cube (132). The patient's multidimensional image cube (132) may be represented in any number of graphical formats such as TIFF, JPEG, EXIF, GIF, BMP, PNG, PPM, PGM, WebP, BAT, BPG, and many others that will occur to those of skill in the art.

According to the example embodiment in FIG. 1, the Central Processing Unit "CPU" (191) connects to a cloud network (124), wherein the network has access to the trained function( ) (180) and converts the patient's multidimensional image cube (132) into a result image plane which can be interpreted through direct observation, pixel quantification, shape recognition, or re-transformation into new multidimensional data planes image cubes to be executed by higher order data functions( ). In another example embodiment disclosed in FIG. 1, the CPU (191) houses storage that contains the trained function( ) (180), and the confidence values (193), for the patient's (170) targeted condition. Another example embodiment disclosed in FIG. 1 is remote access to the trained function( ) (180), and confidence values (182), for the targeted condition.

According to the example embodiment in FIG. 1, confidence values (193) are obtained through testing a specific data function( ) (180) on subjects previously or subsequently known to be normal or abnormal for the targeted condition and made available in the form of sensitivity values, specificity values, predictive values, likelihood values, error values, interval values and other forms of probability statistical measure known or to be known in the art. These confidence values are used in the interpretation of the result data plane by the operator and form the trait based score (192). The trait based score (192) is a relative index of the percentage of likelihood of the condition based upon the assigned function (180) and the assigned functions confidence value (182).

Figure 2:
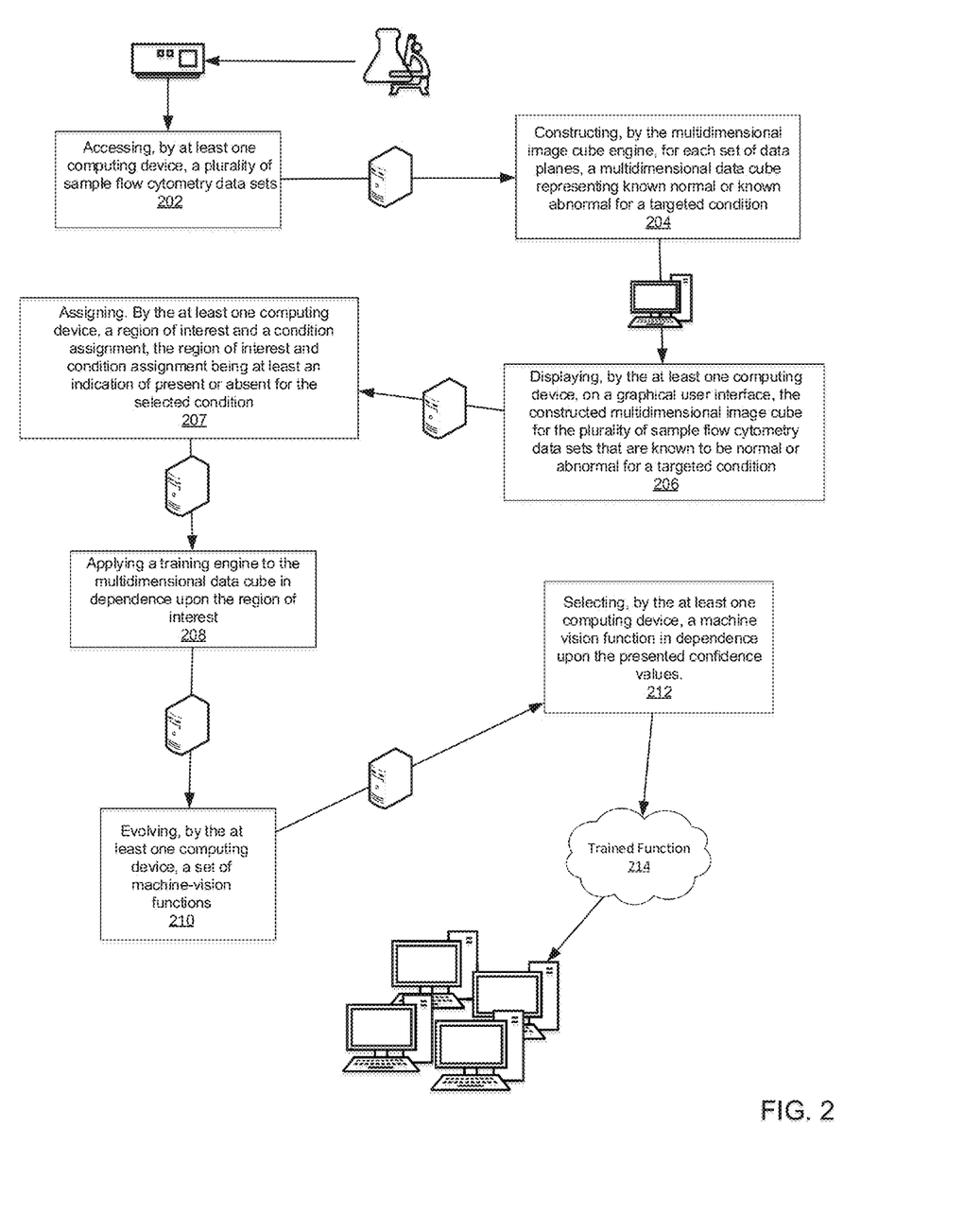
FIG. 2 is an overview of an example method for training a function with multidimensional image cubes from the flow cytometry data.

FIG. 2 sets forth a flow chart and data flow diagram for an example method of training a machine-vision function (214) for use in diagnosing a targeted condition. According to the example method of FIG. 2, a computing device accesses sample flow cytometry data sets (202). The sample flow cytometry sets are of known value for a targeted condition. The known value is attributed to the training engine that begins feature extraction.

The sample flow cytometry data sets (202) serve as input to the multidimensional image cube engine, wherein the flow cytometry data sets (202) are rendered and constructed into a multidimensional image cube (204). The resulting multidimensional image cube (204) is displayed on a computing device, most commonly a GUI (206), wherein the multidimensional image contains sample flow cytometry data sets (202) rendered into a multidimensional image cube that are normal, abnormal, or both for a targeted condition (204).

The multidimensional image cube (204) is then assigned by a pre-training engine a region of interest and a condition assignment (207). The region of interest narrows down the scope or field in which the GA should target and focus on the multidimensional image cube. The condition assignment (207) assigns a condition area on which the training engine should target as either normal or abnormal for the targeted condition. The region selection as well as the condition assignment (207) are optional disclosures but serve i=to decrease computing time and increase confidence values.

The training engine (208) is applied to the multidimensional image cube (204), wherein the training engine (208) executes a dynamically adjusting parameterized inter-plane data function on the multidimensional image cube. According to FIG. 2 an example embodiment of the dynamically adjusting parameterized machine-vision inter-plane data function is disclosed as a Genetic Algorithm "GA" that executes until a confidence value (212) is reached. An example of an application that executes a GA is the GENIE™ software package. GENIE™ is a software system for rapidly evolving feature extraction algorithms for image analysis. In one embodiment GENIE™ is applied as the training engine (208) to the multidimensional image cube (204). GENIE™ executes a GA with input data from the multidimensional image cube until a set of fitness values is reached. The product of GENIE™ results in a machine-vision function (210) that correlates to the confidence value (212) associated with the targeted disease. Meaningful confidence values (212) can be associated with the ethical limits of research for the targeted condition, or may be set by scientific research standards, other standardized based confidence values (212) will occur to those of skill in the art. The resulting chosen machine-vision function (210) is then utilized as the machine-vision trained function (214) that can be applied to the patient's flow cytometry data. The machine-vision trained function (214) in example FIG. 2 resides on a network (124) in which users may access through means such as the Internet to allow wide dispersal and accessibility to the trained function for the targeted condition.

Figure 3:
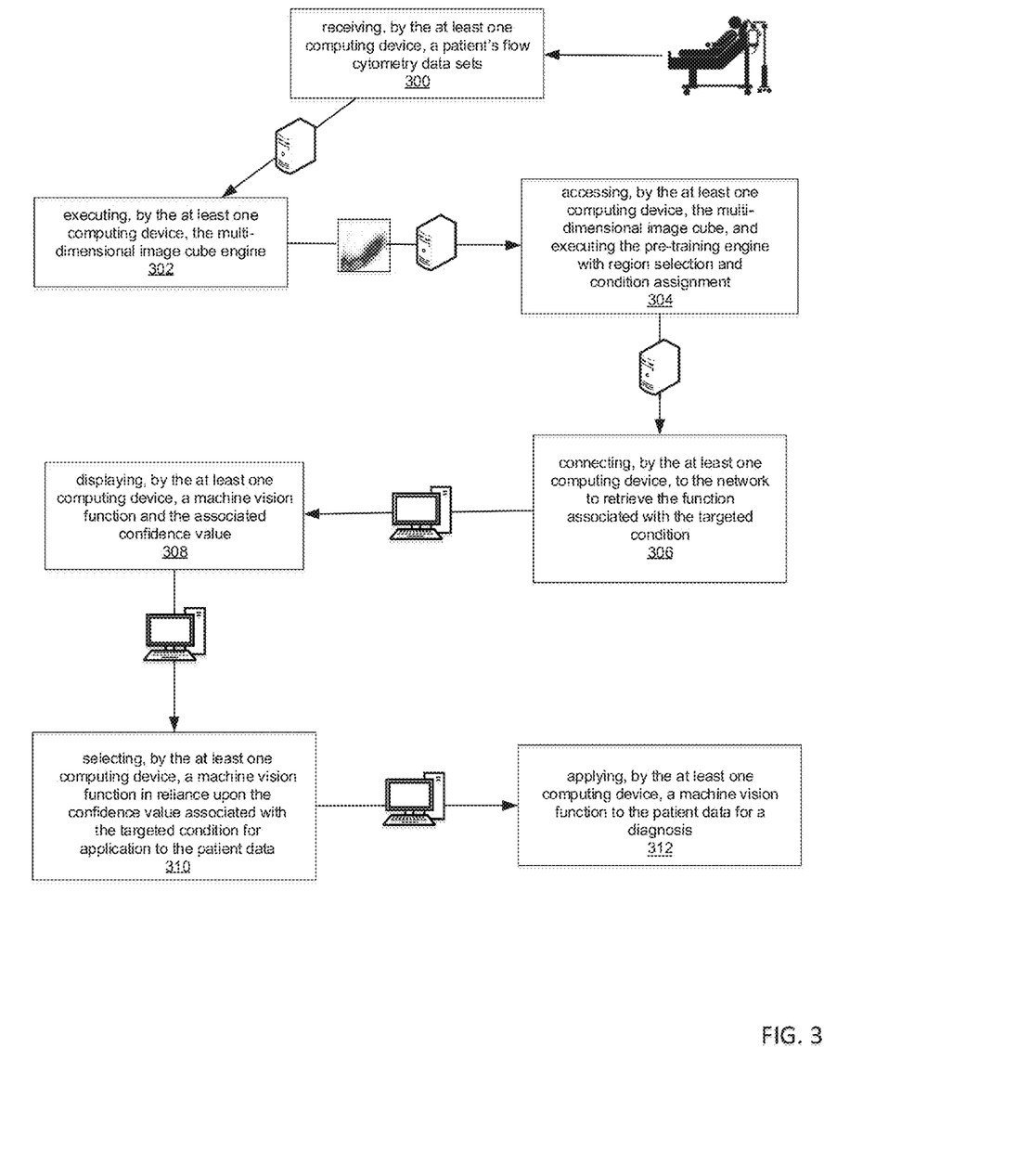
FIG. 3 is an overview of an example method of executing the trained function with a patient's multidimensional image cube from flow cytometry data.

As set forth in FIG. 3 an example embodiment of applying a trained machine-vision function( ) to a patient's flow cytometry data is described herein. A computer (300) configured to receive a patient's flow cytometry data sets and the computer configured to prepare the data for input into the multidimensional image cube Engine (302). The data sets from the patient's flow cytometry data are standard output from flow cytometry data protocols, although other data outputs are possible and will occur to those of skill in the art.

The multidimensional image cube engine (302) prepares the multidimensional image cube for processing by the pre-training engine (304). The pre-training engine (304) accesses the multidimensional image cube (302) and executes a region selection based upon the targeted condition. A region selection function can be used to reduce the area of the multidimensional image cube to an area of focus so that the reliability and confidence values can increase. The region selection can also be executed on the patient's data to improve accuracy after applying the machine-vision function( ).

In one embodiment, a computer is configured to connect to a network (306) to retrieve the machine-vision function( ) that was created by the training engine. The computer is configured to retrieve the associated machine-vision function( ) and its confidence value for processing. In the example embodiment of FIG. 3, processing of the region selected patient multidimensional image cube results in a data plane from which the diagnoses score for a targeted condition is extracted (312). A diagnosis score is a relative health based score for the targeted condition. An example of a diagnosis score or trait based score is generated by calculating the ratio of white pixels to the ratio of black pixels on the result data plane (312). Other variations of a diagnosis score or trait based score are possible and will occur to those of skill in the art.

In an additional example embodiment of FIG. 3, the computer is configured to connect to a local area network (306) to retrieve a machine-vision function. In a further embodiment a computer is configured wherein the machine-vision function is stored locally on readable memory, other forms of access and storage of the repositories for the trained machine-vision function( ) are capable and will occur to those of skill in the art.

In another example embodiment of FIG. 3, the computers data processing unit accesses the machine-vision function for the targeted disease, the computer then displays (308) on a GUI the machine-vision function for user selection and review of the relative confidence values associated with the trained machine-vision function for the targeted disease. The computer by displaying multiple machine-vision functions may be used by a user to select alternative machine-vision functions with lower confidence values depending on the users preference. This allows customization of the trained machine-vision functions and allow for greater breadth of condition diagnosis. In one embodiment the computer is configured to select the best fit machine-vision function associated with the targeted condition (310). The computer in doing so will choose the machine-vision function most closely aligned to the confidence value with the highest correlation. In another embodiment a physician or clinician may select the best fit machine-vision function based upon its relative confidence score.

The best fit machine-vision function( ) is then applied by a computer that is configured with the patients multidimensional image cube consisting of the patients flow cytometry data sets. The computer executes the machine-vision function( ) resulting in a score on matching of the feature based characteristics of the multidimensional cube to the function( ) assigned to a targeted condition. In one embodiment the score is a correlation of how closely the extracted features align with those of the trained machine-vision function data. The feature extracted similarities produce a corresponding score based upon the relative indicators within the trained data and the patient data.

Figure 4:
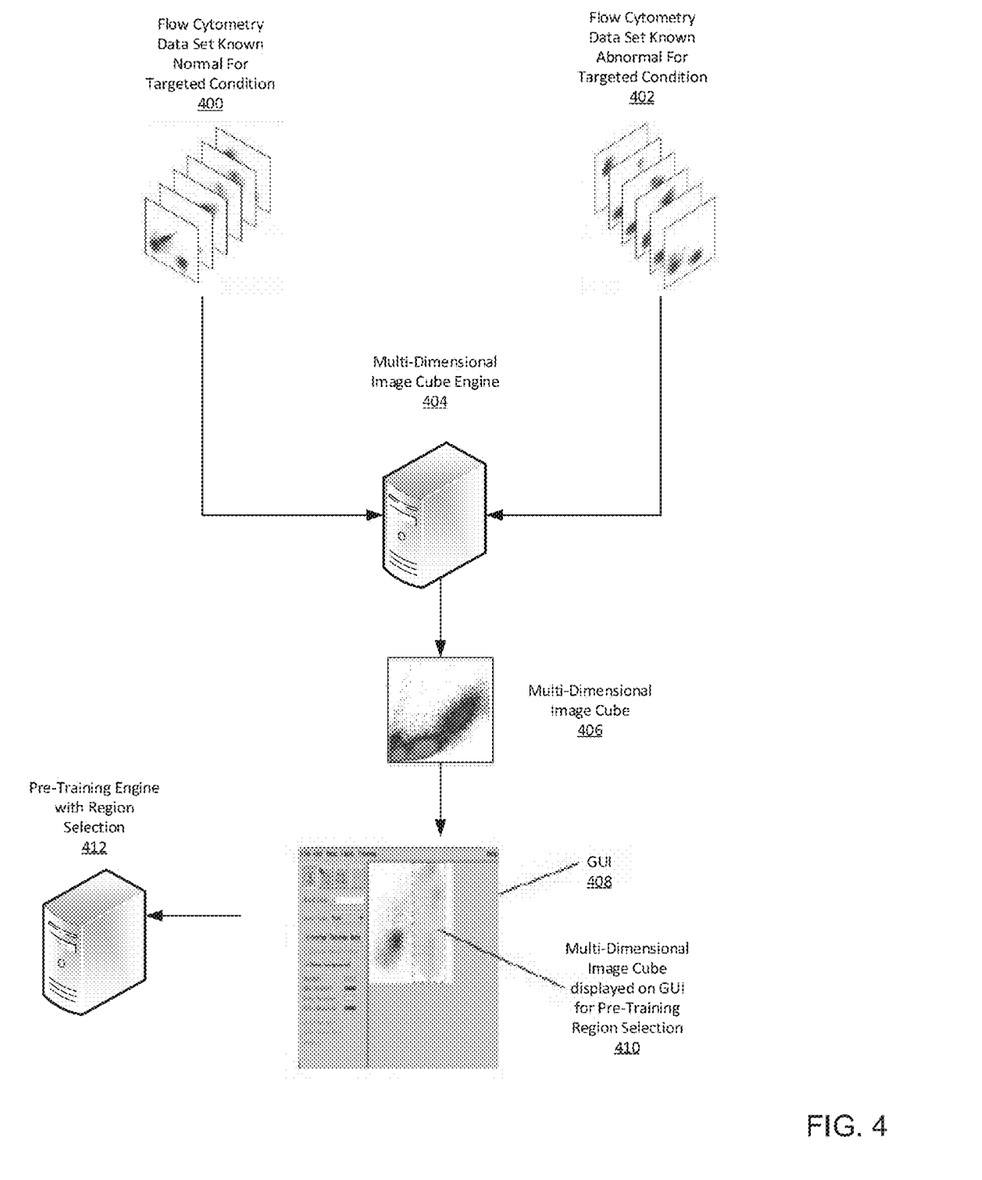
FIG. 4 is an overview of an example method for preparing the multidimensional image cubes for use in the training engine.

FIG. 4 sets forth a flowchart and data flow diagram of an example method for obtaining a multidimensional image cube (406) and a selected region (412) according to embodiments of the present invention. According to the example method of FIG. 4, flow cytometry data from known normal (400) and known abnormal (402) are utilized in the training engine to develop the feature extraction and machine-vision function that corresponds with the targeted condition. The flow cytometry data (400 and 402) are input to the multidimensional image cube Engine (404) that accepts data in formats such as TIFF, JPEG, EXIF, GIF, BMP, PNG, PPM, PGM, WebP, BAT, BPG, and others that will occur to those of skill in the art.

According to example embodiment in FIG. 4, the multidimensional image cube engine (404) produces a multidimensional image cube (406). The multidimensional cube engine (404) constructs the image cube (406) by stacking individual flow cytometry data points on a density plot that is then constructed in the x, y, and z axis. The corresponding image cube contains data from the known normal and abnormal flow cytometry data slides. The resulting multidimensional image cubes (406) are displayed on a computing device configured with a GUI (408). Displaying the multidimensional image cubes (406) are for verification purposes and in another embodiment the multidimensional image cubes (406) are not displayed, but rather processed through the pre-training engine with region selection (412). In either of the described embodiments, the multidimensional cubes are analyzed with a best fit algorithm to remove erroneous data points that were constructed from the flow cytometry data slides. Removal of the erroneous data points is not a required step in the current embodiment, but serves to reduce computing time and increase the confidence value in the resulting machine-vision function.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A method of targeted diagnostic condition analysis from flow cytometry data, the method comprising:
accessing, by at least one computing device, a plurality of sample flow cytometry data sets, wherein the sample flow cytometry data sets include a plurality of flow cytometry data sets that are known to be present for the targeted condition and a plurality of flow cytometry data sets that are known to be absent for the targeted condition; each sample flow cytometry data set including a set of data planes wherein each data plane includes a representation of a particular marker; wherein each data plane includes a flow cytometry image, including at least a set of pixels having a pixel location and a pixel value; constructing, by the at least one computing device, for each set of data planes a multidimensional data cube representing a current condition state; displaying, by the at least one computing device, to a user on a graphical user interface, the set of data planes for the plurality of sample flow cytometry data sets that are known to be present or absent for the targeted condition; assigning, by the at least one computing device, a region of interest and a condition assignment, the region of interest and condition assignment being at least an indication of present or absent for the selected condition;

applying a training engine to the multidimensional data cube in dependence upon the region of interest, wherein applying the training engine includes executing a dynamically adjusting parameterized inter-plane data function to the multidimensional image cube assigned with the region of interest;

presenting, by the at least one computing device, a set of machine-vision functions, wherein the machine-vision functions are the result of executing the dynamically adjusting parameterized inter-plane data function of the multidimensional image cube, and a set of confidence values associated with the machine-vision functions in dependence upon the multidimensional data cubes and assigned region of interest; and selecting, by the at least one computing device, for application to patient data, a machine-vision function in dependence upon the presented confidence values wherein the training engine executes a genetic algorithm as the dynamically adjusting parameterized inter-plane data function, the genetic algorithm executes until a set of confidence values associated with the machine-vision functions that result from executing the training engine are attained.

2. The method of claim 1, wherein applying a training engine further comprises: selecting a multidimensional image cube and executing a dynamically adjusting parameterized inter-plane data function, the dynamic data function checking to adjust parameters to a best fit analysis and then executes the dynamic data function until a defined confidence value is reached.

3. The method of claim 1, wherein constructing the multidimensional data cube further comprises: executing, by the at least one computing device, a multidimensional cube engine, the multidimensional cube engine overlays multiple sets of flow cytometry data, each set of flow cytometry data has at least one pixel location and at least one pixel value associated therewith, the overlay of pixel location and pixel value of the flow cytometry data set results in the multidimensional image cube.

4. The method of claim 1, wherein a set of confidence values is a statistical determination in reliance upon the training engine results from executing the dynamically adjusting parameterized inter-plane data function.

5. A system of targeted diagnostic condition analysis from flow cytometry data, comprising: at least one computing device; and program instructions executable on at least one computing device that, when executed by the at least one computing device, causes the at least one computing device to:

executing, by the at least one computing device, the multidimensional image cube engine, wherein the multidimensional image cube engine accesses the flow cytometry data sets and constructs a multidimensional image cube;

accessing, by at least one computing device, a plurality of sample flow cytometry data sets, wherein the sample flow cytometry data sets include a plurality of flow cytometry data sets that are known to be present for the targeted condition and a plurality of flow cytometry data sets that are known to be absent for the targeted condition; each sample flow cytometry data set including a set of data planes wherein each data plane includes a representation of a particular marker; wherein each data plane includes a flow cytometry image, including at least a set of pixels having a pixel location and a pixel value; constructing, by the at least one computing device, for each set of data planes a multidimensional data cube representing a current condition state; displaying, by the at least one computing device, to a user on a graphical user interface, the set of data planes for the plurality of sample flow cytometry data sets that are known to be present or absent for the targeted condition; assigning, by the at least one computing device, a region of interest and a condition assignment, the region of interest and condition assignment being at least an indication of present or absent for the selected condition;

applying, by the at least one computing device, a training engine to the multidimensional data cube in dependence upon the region of interest, wherein applying the training engine includes executing a dynamically adjusting parameterized inter-plane data function to the multidimensional image cubes assigned with the region of interest;

displaying, by the at least one computing device, a machine vision function, wherein the machine vision function is a result of applying a training engine and executing to a confidence value, a confidence value is the statistical threshold associated with the targeted condition; selecting, by the at least one computing device, a machine vision function for application to the patient data; wherein the training engine executes a genetic algorithm as the dynamically adjusting parameterized inter-plane data function, the genetic algorithm executes until a set of confidence values associated with the machine-vision functions that result from executing the training engine are attained.

6. The system of claim 5, wherein applying a training engine further comprises: selecting, by the at least one computing device, a multidimensional image cube and executing, by the at least one computing device, a dynamically adjusting parameterized inter-plane data function, the dynamic data function checking to adjust parameters to a best fit analysis and then executes, by the at least one computing device, the dynamic data function until a defined confidence value is reached.

7. The system of claim 5, wherein constructing the multidimensional data cube further comprises: overlaying multiple sets of flow cytometry data, each set of flow cytometry data has at least one pixel location and at least one pixel value associated therewith, the overlay of pixel location and pixel value of the flow cytometry data set results in the multidimensional image cube.

8. The system of claim 5, wherein a set of confidence values is a statistical determination in reliance upon the training engine results from executing the dynamically adjusting parameterized inter-plane data function.

* * * * *